(12) United States Patent
Lin et al.

(10) Patent No.: US 11,505,716 B2
(45) Date of Patent: Nov. 22, 2022

(54) AQUEOUS DISPERSION AND AQUEOUS COATING COMPOSITION COMPRISING THE SAME

(71) Applicants: Dow Global Technologies LLC, Midland, MI (US); Rohm and Haas Company, Collegeville, PA (US)

(72) Inventors: Daoshu Lin, Shanghai (CN); Jianming Xu, Shanghai (CN); Shuyu Duan, Shanghai (CN); Jian Zou, Shanghai (CN); James C. Bohling, Lansdale, PA (US)

(73) Assignees: Dow Global Technologies LLC, Midland, MI (US); Rohm and Haas Company, Collegeville, PA (US)

( * ) Notice: Subject to any disclaimer, the term of this patent is extended or adjusted under 35 U.S.C. 154(b) by 453 days.

(21) Appl. No.: 16/628,691

(22) PCT Filed: Jul. 11, 2017

(86) PCT No.: PCT/CN2017/092472
§ 371 (c)(1),
(2) Date: Jan. 6, 2020

(87) PCT Pub. No.: WO2019/010629
PCT Pub. Date: Jan. 17, 2019

(65) Prior Publication Data
US 2020/0181442 A1   Jun. 11, 2020

(51) Int. Cl.
| | |
|---|---|
| C09D 7/65 | (2018.01) |
| C09D 7/20 | (2018.01) |
| C09D 7/63 | (2018.01) |
| C09D 133/06 | (2006.01) |
| C08F 220/18 | (2006.01) |
| A61L 9/04 | (2006.01) |

(52) U.S. Cl.
CPC .......... *C09D 133/062* (2013.01); *A61L 9/042* (2013.01); *C08F 220/1804* (2020.02); *C09D 7/20* (2018.01); *C09D 7/63* (2018.01); *C09D 7/65* (2018.01); *C08K 2201/007* (2013.01)

(58) Field of Classification Search
CPC ........ C09D 133/062; C09D 7/65; C09D 7/20; C09D 7/63; C08F 220/1804; A61L 9/042; C08K 2201/007

USPC .......................................................... 523/102
See application file for complete search history.

(56) References Cited

U.S. PATENT DOCUMENTS

| | | | |
|---|---|---|---|
| 3,399,080 A | 8/1968 | Vitkuske | |
| 3,404,116 A | 10/1968 | Pueschner et al. | |
| 4,020,156 A | 4/1977 | Murray et al. | |
| 4,191,813 A | 3/1980 | Reed et al. | |
| 4,263,407 A | 4/1981 | Reed, Jr. | |
| 4,980,392 A | 12/1990 | Yamamoto | |
| 5,696,199 A * | 12/1997 | Senkus | B01J 20/28042 524/556 |
| 7,153,497 B2 | 12/2006 | Hughes et al. | |

FOREIGN PATENT DOCUMENTS

| | | |
|---|---|---|
| AU | 2006236009 A1 | 5/2007 |
| CN | 101781489 A | 7/2010 |
| CN | 104945987 A | 9/2015 |
| EP | 0121712 B1 | 4/1987 |
| EP | 2006313 A2 | 12/2008 |
| EP | 2860227 A1 | 4/2015 |
| WO | 0162311 A1 | 8/2001 |
| WO | 02089862 A2 | 11/2002 |
| WO | 2009073729 A2 | 6/2009 |
| WO | 2016122843 | 8/2016 |

OTHER PUBLICATIONS

Suppelementary European Search Report for the corresponding European U.S. Appl. No. 17/917,313 dated Jan. 25, 2021; 9 pages.
Pena, B., et al; Characterization of Polysulfone and Polysulfone/Vanillin Microcapsules; American Chemical Society; Applied Material and Sciences; pp. 4420-4430.
Voncina, B,, Vivod, V., Chen, Wen-Tung; Surface Modification of PET Fibers with the Use of b-Cyclodextrin; Journal of Applied Polymer Sciences, pp. 3891-3893.
Lin, Lin-Shu, et al; Pectin Gel Vehicles for Controlled Fragrance Delivery; Taylor & Francis Inc.; pp. 149-157.

* cited by examiner

*Primary Examiner* — Kelechi C Egwim
(74) *Attorney, Agent, or Firm* — Karl E. Stauss; Cantor Colburn LLP (57) ABSTRACT

An aqueous dispersion, an aqueous coating composition comprising the aqueous dispersion, and coatings made therefrom capable of slow release of fragrance.

17 Claims, 1 Drawing Sheet

Figure 1 Fragrance release profile of different paints from 5 to 336 hours

Figure 2 Fragrance release profile of different paints from 144 to 336 hours

AQUEOUS DISPERSION AND AQUEOUS COATING COMPOSITION COMPRISING THE SAME

FIELD OF THE INVENTION

The present invention relates to an aqueous dispersion and an aqueous coating composition comprising the same.

INTRODUCTION

Increasingly stringent policies and regulations for the protection of the environment have led to increased demand for coatings having a low volatile organic compound (VOCs) content. The requirement of low VOC coatings favors waterborne coatings over solvent-borne coatings, since the solvent would be a source of a large quantity of VOCs. Aqueous coating compositions typically comprise polymer dispersions as binders. Lowering VOCs of binders have potential for reduced odor and toxicity, but odorants from coalescents or high boiling point VOCs used in the aqueous coating compositions may result in persistent unpleasant odor. Addition of fragrances into coating compositions can mask the unpleasant odor and also provide a pleasant flavor for coatings made therefrom. The dosage of fragrances needs to be at a level such that the odor is pleasant and it is also desirable that such odor effect can last over extended periods of time. CN101781489B describes a method for preparing paints containing lavender essential oil as a fragrance by first blending the fragrance with a binder, and then adding the resultant mixture to pigment grinds to form the paints. However, release of the fragrance in the paints is too fast to meet the long lasting effect of fragrance.

There is therefore a need for an aqueous fragrance-containing coating composition that enables fragrances to be slowly and continuously released over an extended period of time.

SUMMARY OF THE INVENTION

The present invention provides an aqueous dispersion by combining a fragrance-containing binder with specific polymeric adsorbent particles, which enables coatings made therefrom to gradually release the fragrance over an extended period of time.

In a first aspect, the present invention is an aqueous dispersion, comprising:
(a) fragrance-containing binder particles, and
(b) polymeric adsorbent particles having a D50 particle size of from 1 to 30 microns and a specific surface area of 900 m²/g or more.

In a second aspect, the present invention is a process of preparing an aqueous dispersion. The process comprises,
(i) providing fragrance-containing binder particles wherein the fragrance is included during preparation of the binder; and
(ii) admixing the fragrance-containing binder particles obtained from step (i) with polymeric adsorbent particles having a D50 particle size of from 1 to 30 microns and a specific surface area of 900 m²/g or more.

In a third aspect, the present invention is an aqueous coating composition, comprising: an aqueous dispersion of the first aspect, and a pigment.

In a fourth aspect, the present invention is a method of preparing an aqueous coating composition of the third aspect.

DETAILED DESCRIPTION OF THE INVENTION

Aqueous dispersion or aqueous composition herein means that particles dispersed in an aqueous medium. By "aqueous medium" herein is meant water and from 0 to 30%, by weight based on the weight of the medium, of water-miscible compound(s) such as, for example, alcohols, glycols, glycol ethers, glycol esters, and the like.

"Acrylic" in the present invention includes (meth)acrylic acid, (meth)alkyl acrylate, (meth)acrylamide, (meth)acrylonitrile and their modified forms such as (meth)hydroxyalkyl acrylate. Throughout this document, the word fragment "(meth)acryl" refers to both "methacryl" and "acryl". For example, (meth)acrylic acid refers to both methacrylic acid and acrylic acid, and methyl (meth)acrylate refers to both methyl methacrylate and methyl acrylate.

"Glass transition temperature" or "$T_g$" in the present invention can be measured by various techniques including, for example, differential scanning calorimetry ("DSC") or calculation by using a Fox equation. The particular values of $T_g$ reported herein are those calculated by using the Fox equation (T. G. Fox, Bull. Am. Physics Soc., Volume 1, Issue No. 3, page 123 (1956)). For example, for calculating the $T_g$ of a copolymer of monomers $M_1$ and $M_2$, $$\frac{1}{T_g(calc.)} = \frac{w(M_1)}{T_g(M_1)} + \frac{w(M_2)}{T_g(M_2)},$$

wherein $T_g(calc.)$ is the glass transition temperature calculated for the copolymer, $w(M_1)$ is the weight fraction of monomer $M_1$ in the copolymer, $w(M_2)$ is the weight fraction of monomer $M_2$ in the copolymer, $T_g(M_1)$ is the glass transition temperature of the homopolymer of monomer $M_1$, and $T_g(M_2)$ is the glass transition temperature of the homopolymer of monomer $M_2$, all temperatures being in K. The glass transition temperatures of the homopolymers may be found, for example, in "Polymer Handbook", edited by J. Brandrup and E. H. Immergut, Interscience Publishers.

"Polymerized units", also known as "structural units", of the named monomer, refers to the remnant of the monomer after polymerization. That is, a polymer comprising, as polymerized units, of the named monomer means the polymer comprising, in polymerized form, the named monomer.

The polymeric adsorbent particles useful in the present invention comprise a polymer. The polymer in the polymeric adsorbent particle can be a porous crosslinked polymer. The crosslinked polymer matrix may be further crosslinked by subsequent alkylene bridging (post-crosslinking). The polymer in the polymeric adsorbent particles may comprise, as polymerized units, one or more vinyl aromatic monomers and optionally one or more monovinyl aliphatic monomers.

The vinyl aromatic monomer useful for preparing the polymer in the polymeric adsorbent particles may be selected from the group consisting of at least one monovinyl aromatic monomer and at least one polyvinyl aromatic monomer. The vinyl aromatic monomer may be used in an amount of 75% or more, 80% or more, 85% or more, 90% or more, 95% or more, 99% or more, or even 100%, by weight based on the weight of the polymer (i.e., dry weight of the polymeric adsorbent particle).

The monovinyl aromatic monomers useful in preparing the polymer in the polymeric adsorbent particles may include styrene, α-substituted styrene such as methyl styrene, ethyl styrene, t-butyl styrene, bromo styrene; vinyltoluenes, ethyl vinylbenzenes, vinylnaphthalenes, and heterocyclic monomers such as vinylpyridine, or mixtures thereof. Mixtures of monovinyl aromatic monomers can be employed. Preferred monovinyl aromatic monomers include styrene, ethyl vinylbenzene, or mixtures thereof.

The polyvinyl aromatic monomers, that is, crosslinking agents, useful for preparing the polymer in the polymeric adsorbent particles may include divinylbenzene, trivinyl benzene and divinylnaphthalene, and preferably, divinylbenzene. Mixtures of polyvinylbenzene monomers can be employed. The polyvinyl aromatic monomer is used to crosslink the polymer. The vinyl aromatic monomer may comprise 10% or more, 20% or more, 30% or more, 40% or more, 50% or more, 75% or more, 90% or more, or even 100%, of the polyvinyl aromatic monomers; and the rest being the monovinyl aromatic monomers.

The monovinyl aliphatic monomer useful in preparing the polymer in the polymeric adsorbent particles may include esters of (meth)acrylic acids, esters of itaconic acid, esters of maleic acid, acrylonitrile and mixtures thereof. Preferred monovinyl aliphatic monomers include methyl methacrylate, acrylonitrile, ethyl acrylate, 2-hydroxyethyl methacrylate and mixtures thereof. The polymer in the polymeric adsorbent particles may comprise as polymerized units, by weight based on the weight of the polymer, from 0 to 25% of the monovinyl aliphatic monomer, for example, less than 20%, less than 15%, less than 10%, less than 5%, or less than 1% of the monovinyl aliphatic monomer, preferably substantially free of the monovinyl aliphatic monomer.

In some embodiments, the polymeric adsorbent particles comprise a porous crosslinked polymer comprising as polymerized units, by weight based on the weight of the porous crosslinked polymer, from 0 to 90% of the monovinyl aromatic monomer, from 10% to 100% of the polyvinyl aromatic monomer, and from 0 to 25% of the monovinyl aliphatic monomer. In some further embodiments, the polymeric adsorbent particles comprise an alkylene bridged porous crosslinked polymer described above, for example, a methylene bridged porous crosslinked polymer described above. In one preferred embodiment, the polymeric adsorbent particles useful in the present invention comprise a methylene bridged copolymer of divinylbenzene and a monovinyl aromatic monomer.

The polymer in the polymeric adsorbent may be prepared by free radical polymerization, preferably suspension polymerization. The polymer may be porogen-modified, that is, prepared by forming a suspension of a monomer mixture within an agitated, continuous suspending medium in the presence of a porogenic solvent or a mixture of such solvent, followed by polymerization of the monomer or monomer mixture. The monomer mixture refers to the mixture of the monomers described above as the polymerized units of the polymer. Porogenic solvents are inert solvents that are suitable for forming pores and/or displacing polymer chains during polymerization. A porogenic solvent is one that dissolves the monomer mixture being polymerized but does not dissolve the polymer obtained therefrom. Examples of such porogenic solvents include aliphatic hydrocarbon compounds such as heptane and octane, aromatic compounds such as benzene, toluene, and xylene, halogenated hydrocarbon compounds such as dichloroethane and chlorobenzene, and linear polymer compounds such as polystyrene. These compounds may be used alone or as a mixture of two or more thereof. Preferred porogenic solvent is toluene. The amount of the porogenic solvent used in the present invention may be from 30 to 300 parts by weight, preferably from 75 to 250 parts by weight, per 100 parts by weight of the monomer mixture for preparing the polymer in the polymeric adsorbent particles.

Suspension polymerization process is well known to those skilled in the art and may comprise suspending droplets of the monomer or monomer mixture and of the porogenic solvent in a medium in which neither are soluble. This may be accomplished by adding the monomer or monomer mixture and the porogenic solvent with any additives to the suspending medium which contains a dispersing or suspending agent. Preferred suspending medium is water. Preferred suspending agent is a suspension stabilizer, for example, gelatin, polyvinyl alcohol or a cellulosic such as hydroxyethyl cellulose, methyl cellulose or carboxymethyl methyl cellulose, or mixtures thereof. The polymerization process may be conducted in the presence of a free radical initiator. Examples of suitable free radical initiators include organic peroxides such as benzoyl peroxide and lauroyl peroxide, organic azo compounds such as azobisisobutyronitrile, or mixtures thereof. The free radical initiator may be used in an amount of from 0.01 to 10 parts by weight per 100 parts by weight of the monomer mixture for preparing the polymer. Polymerization is typically carried out at temperatures ranging from 15 to 160° C., preferably from 50 to 90° C. The polymer obtained from the polymerization process may be isolated by filtration, optionally washed with one or more solvents include tetrahydrofuran, methanol and water. The resultant polymer may be further dried to obtain beads with a particle size of from 100 to 2,000 µm. The particle size of such beads can be determined automatically by using RapidVue Beckman Coulter equipment. The principle of the test method is that the particles passing through the sensor partially block a beam of light focused on a photodiode, producing electrical pulses whose amplitude is proportional to the particle size. These pulses are applied to the counting circuits (channels, bins) within the counter and therefore the particle size is recorded. Examples of commercially available polymeric adsorbent beads include DOWEX OPTIPORE™ L-493, V-503, and SD-2 polymeric adsorbent beads all available from The Dow Chemical Company (OPTIPORE is a trademark of The Dow Chemical Company), and CHROMABOND HR-P polymeric adsorbent beads available from Macherey Nagel.

The resultant polymeric adsorbent beads may be subjected to additional alkylene bridging (post-crosslinked) of individual polymer chains after polymerization in a swollen state in the presence of a Friedel-Crafts catalyst to introduce rigid microporosity (pores with a diameter less than about 20 Å) into the polymer, thus to form alkylene bridged crosslinked polymer. Post-crosslinking of the polymeric adsorbent beads while it is in a swollen state displaces and rearranges adjacent polymer chains, thereby causing an increase in the number of micropores. This rearrangement serves to increase overall porosity and surface area of the polymer, while also decreasing the average pore size. Post-crosslinking also serves to impart rigidity to the polymer structure, which is useful for providing enhanced physical and dimensional stability to the polymer. Post-crosslinking may be achieved by haloalkylating or acylating the porous crosslinked polymer by reacting with a polyfunctional alkylating or acylating agent, swelling the resulting haloalkylated polymer with an swelling agent, and thereafter maintaining the swollen, haloalkylated polymer at a temperature and in the presence of a Friedel-Crafts catalyst such that haloalkyl or acyl moieties on the polymer react with an aromatic ring of an adjacent polymer chain to form an alkylene bridging moiety. Friedel-Crafts catalysts are Lewis acids and include, for example, $AlCl_3$, $FeCl_3$, $BF_3$ and HF. $AlCl_3$ and $FeCl_{13}$ are preferred. In the instances where the porous crosslinked polymer is, for example, a polymer of styrene, vinylbenzyl chloride and divinylbenzene, the haloalkylation or acylation of the polymer is not necessary. In those instances, the polymer is swollen with a swelling agent and post-crosslinked in the swollen condition to obtain the bridging moieties. The post-crosslinking methods are described in U.S. Pat. Nos. 4,191,813 and 4,263,407, and WO2016/122843A2.

These polymeric adsorbent beads obtained above can be further subjected to any known particle size reduction means including, for example, crushing, grinding, chopping and milling such as ball milling and ultracentrifugal milling, to give the polymeric adsorbent particles useful in the present invention with desirable particle size. Preferably, the polymeric adsorbent particles are employed with powder by dry grinding. Prior to dry grinding, the polymeric adsorbent beads preferably further dry to achieve a water content as low as possible, for example, 5% by weight or less, or 2% by weight or less of water in the dried polymeric adsorbent beads.

The polymeric adsorbent particles useful in the present invention may have a D50 particle size of 0.1 micrometer (microns) or larger. The polymeric adsorbent particles may have a D50 particle size of 30 microns or smaller, 20 microns or smaller, 10 microns or smaller, or even 5 microns or smaller. When particles have a D50 particle size of a certain value, then 50 percent of the particles by volume is composed of particles having diameter less than or equal to that certain value. The D50 particle size may be measured according to the test method described in the Examples section below. The polymeric adsorbent particles useful in the present invention may have a specific surface area of 900 $m^2/g$ or more, 950 $m^2/g$ or more, or even 1,000 $m^2/g$ or more. The polymeric adsorbent particles preferably have a specific surface area of 2,000 $m^2/g$ or less, 1,500 $m^2/g$ or less, 1,300 $m^2/g$ or less, or even 1,100 $m^2/g$ or less. Values of the specific surface area per unit weight of dry polymeric adsorbent particles ($m^2$ per gram of the dry polymeric adsorbent particles) may be determined by the nitrogen adsorption method in which dried and degassed samples are analyzed on an automatic volumetric sorption analyzer. The instrument works on the principle of measuring the volume of gaseous nitrogen adsorbed by a sample at a given nitrogen partial pressure. The volumes of gas adsorbed at various pressures are used in the BET model for the calculation of the surface area of the sample. The specific surface area may be measured according to the test method described in the Examples section below.

The aqueous dispersion of the present invention further comprises fragrance-containing binder particles, preferably in the form of an aqueous dispersion. The binder useful in the present invention is typically an emulsion polymer. The binder may include an acrylic binder, a styrene acrylic binder, a vinyl acrylic binder, or mixtures thereof.

The binder useful in the present invention may comprise, as polymerized units, one or more monoethylenically unsaturated nonionic monomers. As used herein, the term "nonionic monomer" means that a monomer does not bear an ionic charge between pH=1-14. Suitable examples of the polymerizable ethylenically unsaturated nonionic monomers include (meth)acrylic ester monomers, i.e., methacrylic ester or acrylic ester monomers including methyl acrylate, ethyl acrylate, butyl acrylate, 2-ethylhexyl acrylate, decyl acrylate, lauryl acrylate, methyl methacrylate, butyl methacrylate, isodecyl methacrylate, and lauryl methacrylate; (meth)acrylonitrile; styrene and substituted styrene such as α-methyl styrene, and vinyl toluene; butadiene; ethylene; propylene; α-olefin such as 1-decene; vinyl esters such as vinyl acetate, vinyl butyrate, and vinyl versatate; and other vinyl monomers such as vinyl chloride and vinylidene chloride. The binder may comprise as polymerized units, based on the dry weight of the binder, from 90% to 100% by weight, from 92% to 99% by weight, or from 94% to 98% by weight, of the monoethylenically unsaturated nonionic monomers.

The binder useful in the present invention may further comprise, as polymerized units, one or more ethylenically unsaturated monomers having one or more functional groups. The functional groups may be selected from a carbonyl, acetoacetoxy, acetoacetamide, alkoxysilane, ureido, amide, imide, amino, carboxyl, or phosphorous group. Examples of such functional-group-containing ethylenically unsaturated monomer may include α, β-ethylenically unsaturated carboxylic acids including an acid-bearing monomer such as methacrylic acid, acrylic acid, itaconic acid, maleic acid, or fumaric acid; or a monomer bearing an acid-forming group which yields or is subsequently convertible to, such an acid group (such as anhydride, (meth)acrylic anhydride, or maleic anhydride); vinyl phosphonic acid, allyl phosphonic acid, phosphoalkyl (meth)acrylates such as phosphoethyl (meth)acrylate, phosphopropyl (meth)acrylate, phosphobutyl (meth)acrylate, or salts thereof; 2-acrylamido-2-methyl-1-propanesulfonic acid; sodium salt of 2-acrylamido-2-methyl-1-propanesulfonic acid; ammonium salt of 2-acrylamido-2-methyl-1-propane sulfonic acid; sodium vinyl sulfonate; sodium styrene sulfonate; sodium salt of allyl ether sulfonate; and the like; diacetone acrylamide (DAAM), acrylamide, methacrylamide, monosubstituted (meth)acrylamide, N-methylacrylamide, N-ethylacrylamide, N-isopropylacrylamide, N-butylacrylamide, N-tertiary butylacrylamide, N-2-ethylhexylacrylamide, N,N-dimethylacrylamide, N,N-diethylacrylamide, methylacrylamidoethyl ethylene urea, vinyl trimethoxyl silane, 3-Methacryloxypropyltrimethoxysilane, or mixtures thereof. The functional-group-containing ethylenically unsaturated monomer preferably is the ethylenically unsaturated monomer having at least one acetoacetoxy or acetoacetamide functional group. Preferred functional-group-containing ethylenically unsaturated monomer is selected from the group consisting of acrylic acid, methacrylic acid, acrylamide, acetoacetoxyethyl methacrylate (AAEM), phosphoethyl (meth)acrylate, and sodium salt of 2-acrylamido-2-methyl-1-propanesulfonic acid. The binder may comprise as polymerized units, based on the dry weight of the binder, from 0.1% to 20% by weight, from 0.3% to 10% by weight, from 0.5% to 5% by weight, or from 1% to 3% by weight, of such functional-group-containing ethylenically unsaturated monomer.

The binder useful in the present invention may also comprise, as polymerized units, one or more multiethylenically unsaturated nonionic monomers. Examples of suitable multiethylenically unsaturated nonionic monomers may include allyl methacrylate, tripropylene glycol dimethacrylate, diethylene glycol dimethacrylate, ethylene glycol dimethacrylate, 1,6-hexanediol dimethacrylate, 1,3-butylene glycol dimethacrylate, polyalkylene glycol dimethacrylate, diallyl phthalate, trimethylolpropane trimethacrylate, divinylbenzene, divinyltoluene, trivinylbenzene, divinylnaphthalene, or mixtures thereof. The binder may comprise as polymerized units, by weight based on the dry weight of the binder, from 0.01% to 1% or from 0.1% to 0.5%, of the multiethylenically unsaturated nonionic monomer.

The types and levels of the monomers described above for preparing the binder may be chosen to provide the binder with a glass transition temperature ($T_g$) in the range of from −50° C. to 100° C., from −30° C. to 50° C., from −10° C. to 40° C., or from 0° C. to 30° C.

Fragrances (also known as flavors) in the fragrance-containing binder generally comprise natural and synthetic oils which give off a characteristic pleasant odor. Both synthetic and natural flavor oils derived from plants, leaves, flowers, fruits and so forth and combinations thereof may be utilized in the present invention. The fragrance ingredients are selected based on the intended use of the coatings and the coatings' desired aroma. Examples of fragrance compounds useful in the present invention include hexyl cinnamic aldehyde; amyl cinnamic aldehyde; amyl salicylate; hexyl salicylate; terpineol; 3,7-dimethyl-cis-2,6-octadien-1-ol; 2,6-dimethyl-2-octanol; 2,6-dimethyl-7-octen-2-ol; 3,7-dimethyl-3-octanol; 3,7-dimethyl-trans-2,6-octadien-1-ol; 3,7-dimethyl-6-octen-1-ol; 3,7-dimethyl-1-octanol; 2-methyl-3-(para-tert-butylphenyl)-propionaldehyde; 4-(4-hydroxy-4-methylpentyl)-3-cyclohexene-1-carboxaldehyde; tricyclodecenyl propionate; tricyclodecenyl acetate; anisaldehyde; 2-methyl-2-(para-iso-propylphenyl)-propionaldehyde; ethyl-3-methyl-3-phenyl glycidate; 4-(para-hydroxyphenyl)-butan-2-one; 1-(2,6,6-trimethyl-2-cyclohexen-1-yl)-2-buten-1-one; para-methoxyacetophenone; para-methoxy-alpha-phenylpropene; methyl-2-n-hexyl-3-oxo-cyclopentane carboxylate; undecalactone gamma, geraniol; geranyl acetate; linalool; linalyl acetate; tetrahydrolinalool; citronellol; citronellyl acetate; dihydromyrcenol; dihydromyrcenyl acetate; tetrahydromyrcenol; terpinyl acetate; nopol; nopyl acetate; 2-phenylethanol; 2-phenylethyl acetate; benzyl alcohol; benzyl acetate; benzyl salicylate; benzyl benzoate; styrallyl acetate; dimethylbenzylcarbinol; trichloromethylphenylcarbinyl methylphenylcarbinyl acetate; isononyl acetate; vetiveryl acetate; vetiverol; 2-methyl-3-(p-tert-butylphenyl)-propanal; 2-methyl-3-(p-isopropylphenyl)-propanal; 3-(p-tert-butylphenyl)-propanal; 4-(4-methyl-3-pentenyl)-3-cyclohexenecarbaldehyde; 4-acetoxy-3-pentyltetrahydropyran; methyl dihydrojasmonate; 2-n-heptylcyclopentanone; 3-methyl-2-pentyl-cyclopentanone; n-decanal; n-dodecanal; 9-decenol-1; phenoxy ethyl isobutyrate; phenylacetaldehyde dimethylacetal; phenylacetaldehyde diethylacetal; geranonitrile; citronellonitrile; cedryl acetal; 3-isocamphylcyclohexanol; cedryl methylether; isolongifolanone; aubepine nitrile; aubepine; heliotropine; eugenol; vanillin; diphenyl oxide; hydroxycitronellal ionones; methyl ionones; isomethyl ionomes; irones; cis-3-hexenol and esters thereof; indane musk fragrances; tetralin musk fragrances; isochroman musk fragrances; macrocyclic ketones; macrolactone musk fragrances; ethylene brassylate; and mixtures thereof.

The fragrance-containing binder particles may comprise the fragrance in an amount of 0.0001% or more, 0.001% or more, 0.01% or more, 0.1% or more, or even 0.3% or more, and at the same time, 2% or less, 1% or less, 0.8% or less, or even 0.5% or less, by weight based on the dry weight of the fragrance-containing binder.

The fragrance-containing binder useful in the present invention may be prepared by polymerization, preferably emulsion polymerization, of the monomers that constitute polymerized units of the binder, where the fragrance may be included during any stage of preparation of the binder, for example, prior to, during or after the polymerization of the monomers, preferably when reactor temperature for preparation of the binder is 50° C. or above. Preferably, the fragrance-containing binder is obtained by polymerization of the monomers in an aqueous medium in the presence of the fragrance. For example, the fragrance is firstly mixed with the monomer emulsion, and then the resultant mixture is gradually fed into a reactor. The monomers may be added neat or as an emulsion in water; or added in one or more additions or continuously, linearly or nonlinearly, over the reaction period of preparing the binder. The fragrance may be added prior to or during the polymerization of the monomers, or combinations thereof. In one embodiment, the fragrance is mixed with the monomer emulsion prior to polymerization of the monomers to obtain the fragrance-containing binder particles. Conditions of emulsion polymerization are known in the art, for example, U.S. Pat. Nos. 3,399,080 and 3,404,116. Multistage free-radical polymerization can also be used in preparing the binder, which at least two stages are formed sequentially, and usually results in the formation of the multistage polymer comprising at least two polymer compositions. The polymerization process typically gives an aqueous dispersion of binder particles. The fragrance-containing binder particles may have an average particle size of from 50 to 500 nanometers (nm), from 80 to 300 nm, from 100 to 200 nm, or from 110 to 180 nm. The average particle size herein refers to the number (D-90) average particle size as measured by Brookhaven BI-90 Particle Size Analyzer.

The fragrance-containing binder particles are mixed with the polymeric adsorbent particles to form the aqueous dispersion of the present invention. The polymeric adsorbent particles may be present, by dry weight based on the dry weight of the fragrance-containing binder particles, in an amount of 0.1% or more, 0.3% or more, 0.6% or more, 0.8% or more, or even 1% or more, and at the same time, 6% or less, 5% or less, 4% or less, 3% or less, or even 2% or less.

The aqueous dispersion of the present invention may have a pigment volume concentration (PVC) of less than 15%, less than 10%, or even less than 5%. PVC in the present invention may be determined according to the following equation:

$$\text{PVC \%} = [\text{Volume}_{(Pigment+Extender+polymeric\ adsorbent)} / \text{Volume}_{(Pigment+Extender+polymeric\ adsorbent+Binder)}] \times 100\%$$

The present invention also relates to an aqueous coating composition comprising the aqueous dispersion of the present invention. The aqueous coating composition may also comprise pigments to form pigmented coating compositions (also known as "paint formulations"). "Pigment" herein refers to a particulate inorganic material which is capable of materially contributing to the opacity or hiding capability of a coating. Such materials typically have a refractive index greater than 1.8. The pigments may include, for example, titanium dioxide ($TiO_2$), zinc oxide, iron oxide, zinc sulfide, barium sulfate, barium carbonate, or mixture thereof. In a preferred embodiment, pigment used in the present invention is $TiO_2$. $TiO_2$ typically exists in two crystal forms, anastase and rutile. $TiO_2$ may be also available in concentrated dispersion form. The aqueous coating composition may also comprise one or more extenders. "Extender" herein refers to a particulate inorganic material having a refractive index of less than or equal to 1.8 and greater than 1.3. Examples of suitable extenders include calcium carbonate, clay, calcium sulfate, aluminosilicates, silicates, zeolites, mica, diatomaceous earth, solid or hollow glass, ceramic beads, nepheline syenite, feldspar, diatomaceous earth, calcined diatomaceous earth, talc (hydrated magnesium silicate), silica, alumina, kaolin, pyrophyllite, perlite, baryte, wollastonite, opaque polymers such as ROPAQUE™ Ultra E available from The Dow Chemical Company (ROPAQUE is a trademark of The Dow Chemical Company), or mixtures thereof. The aqueous coating composition may have a PVC of from 5% to 90%, from 10% to 85%, or from 15% to 80%.

The aqueous coating composition of the present invention may further comprise one or more defoamers. "Defoamers" herein refer to chemical additives that reduce and hinder the formation of foam. Defoamers may be silicone-based defoamers, mineral oil-based defoamers, ethylene oxide/propylene oxide-based defoamers, alkyl polyacrylates, or mixtures thereof. Suitable commercially available defoamers include, for example, TEGO Airex 902 W and TEGO Foamex 1488 polyether siloxane copolymer emulsions both available from TEGO, BYK-024 silicone deformer available from BYK, or mixtures thereof. The concentration of the defoamer may be, based on the total dry weight of the aqueous coating composition, generally from 0 to 2% by weight, from 0.1% to 1% by weight, or from 0.2% to 0.5% by weight.

The aqueous coating composition of the present invention may further comprise one or more thickeners. The thickeners may include polyvinyl alcohol (PVA), clay materials, acid derivatives, acid copolymers, urethane associate thickeners (UAT), polyether urea polyurethanes (PEUPU), polyether polyurethanes (PEPU), or mixtures thereof. Examples of suitable thickeners include alkali swellable emulsions (ASE) such as sodium or ammonium neutralized acrylic acid polymers; hydrophobically modified alkali swellable emulsions (HASE) such as hydrophobically modified acrylic acid copolymers; associative thickeners such as hydrophobically modified ethoxylated urethanes (HEUR); and cellulosic thickeners such as methyl cellulose ethers, hydroxymethyl cellulose (HMC), hydroxyethyl cellulose (HEC), hydrophobically-modified hydroxy ethyl cellulose (HMHEC), sodium carboxymethyl cellulose (SCMC), sodium carboxymethyl 2-hydroxyethyl cellulose, 2-hydroxypropyl methyl cellulose, 2-hydroxyethyl methyl cellulose, 2-hydroxybutyl methyl cellulose, 2-hydroxyethyl ethyl cellulose, and 2-hdoxypropyl cellulose. Preferably, the thickener is a hydrophobically-modified hydroxy ethyl cellulose (HMHEC). The concentration of the thickener may be, based on the total dry weight of the aqueous coating composition, generally from 0 to 1% by weight, from 0.1% to 0.8% by weight, or from 0.2% to 0.6% by weight.

The aqueous coating composition of the present invention may further comprise one or more wetting agents. "Wetting agents" herein refer to chemical additives that reduce the surface tension of a coating composition, causing the coating composition to more easily spread across or penetrate the surface of a substrate. Wetting agents may be polycarboxylates, anionic, zwitterionic, or non-ionic. The concentration of the wetting agent may be, based on the total dry weight of the aqueous coating composition, from 0 to 1% by weight, from 0.1% to 0.8% by weight, or from 0.2% to 0.6% by weight.

The aqueous coating composition of the present invention may further comprise one or more coalescents. "Coalescents" herein refer to slow-evaporating solvents that fuse polymer particles into a continuous film under ambient condition. Examples of suitable coalescents include 2-n-butoxyethanol, dipropylene glycol n-butyl ether, propylene glycol n-butyl ether, dipropylene glycol methyl ether, propylene glycol methyl ether, propylene glycol n-propyl ether, diethylene glycol monobutyl ether, ethylene glycol monobutyl ether, ethylene glycol monohexyl ether, triethylene glycol monobutyl ether, dipropylene glycol n-propyl ether, n-butyl ether, or mixtures thereof. Preferred coalescents include dipropylene glycol n-butyl ether, ethylene glycol monobutyl ether, diethylene glycol monobutyl ether, n-butyl ether, or mixtures thereof. The concentration of the coalescent may be, based on the total dry weight of the aqueous coating composition, from 0 to 3% by weight, from 0.1% to 2% by weight, or from 0.2% to 1.5% by weight.

In addition to the components described above, the aqueous coating composition of the present invention may further comprise any one or combination of the following additives: buffers, neutralizers, humectants, mildewcides, biocides, anti-skinning agents, colorants, flowing agents, anti-oxidants, plasticizers, leveling agents, thixotropic agents, adhesion promoters, and grind vehicles. When present, these additives may be present in a combined amount of from 0 to 2% by weight, from 0.1% to 1.5% by weight, or from 0.2% to 1.0% by weight, based on the total weight of the aqueous coating composition.

The aqueous coating composition of the present invention may further comprise water. The concentration of water may be, by weight based on the total weight of the coating composition, from 30% to 90%, from 40% to 80%, or from 50% to 70%.

The aqueous coating composition of the present invention may be prepared by admixing the aqueous dispersion of the present invention with other optional components, e.g., pigments and/or extenders as described above. When preparing the aqueous coating composition, the polymeric adsorbent particles are first mixed with the fragrance-containing binder particles to form the aqueous dispersion of the present invention, which is then mixed with other components, e.g., pigment. Other components in the aqueous coating composition may be mixed in any order to provide the aqueous coating composition of the present invention. In some embodiments, when the aqueous coating composition comprises pigment and/or extender, the process of preparing the aqueous coating composition of the present invention comprises, providing the aqueous dispersion of the present invention; forming grinds comprising pigment and/or extender, preferably forming a slurry of pigment and/or extender; and mixing the grinds and the aqueous dispersion. Such process of preparing the aqueous coating composition by using the aqueous dispersion of the present invention surprisingly provides the obtained coatings with better controlled release for fragrance as compared to processes where the fragrance and the polymeric adsorbent particles are post added during preparation of grinds or after paint preparation.

The aqueous coating composition of the present invention can be applied to, and adhered to, various substrates, comprising applying the aqueous coating composition to a substrate, and drying, or allowing to dry, the applied aqueous coating composition to form a coating. Examples of suitable substrates include wood, metals, plastics, foams, stones, elastomeric substrates, glass, fabrics, concrete, or cementitious substrates. The coating composition, preferably comprising the pigment, is suitable for various applications such as marine and protective coatings, automotive coatings, traffic paint, Exterior Insulation and Finish Systems (EIFS), roof mastic, wood coatings, coil coatings, plastic coatings, powder coatings, can coatings, architectural coatings, and civil engineering coatings. The coating composition is particularly suitable for architectural coatings.

The aqueous coating composition of the present invention can be applied to a substrate by incumbent means including brushing, dipping, rolling and spraying. The aqueous coating composition is preferably applied by spraying. The standard spray techniques and equipment for spraying such as air-atomized spray, air spray, airless spray, high volume low pressure spray, and electrostatic spray such as electrostatic bell application, and either manual or automatic methods can be used. After the coating composition of the present invention has been applied to a substrate, the coating composition can dry, or allow to dry, to form a film (this is, coating) at room temperature (20-25° C.), or at an elevated temperature, for example, from 35° C. to 60° C., and then, the fragrance is capable of being released from the coating over an extended period of time. The extended period of time may be greater than 7 days, 14 days, 28 days, 180 days or even 360 days. The aqueous coating composition can provide better controlled release profile of fragrance than conventional coating compositions that does not comprise the aqueous dispersion of the present invention. For example, the coatings made therefrom first demonstrates slow release rate and then continuous fragrance release thereafter over the extended period of time.

EXAMPLES

Some embodiments of the invention will now be described in the following Examples, wherein all parts and percentages are by weight unless otherwise specified.

The following OPTIPORE and AMBERLITE adsorbents are all available from The Dow Chemical Company:

DOWEX OPTIPORE L493 adsorbent ("L493") is an alkylene bridged copolymer of styrene and divinylbenzene copolymer (surface area: 1100 $m^2/g$, particle size: 280-900 µm).

DOWEX OPTIPORE SD-2 adsorbent ("SD-2") is a dimethylamine functionalized alkylene bridged copolymer of styrene and divinylbenzene (surface area: 1100 $m^2/g$, particle size: 280-900 µm).

AMBERLITE XAD1180 adsorbent ("XAD1180") is a non methylene-bridged highly crosslinked styrenic polymeric adsorbent (surface area: 500 $m^2/g$, particle size: 350-600 µm).

Zeolite is available from Sigma-Aldrich.

Styrene ("ST") is available from Langyuan Chemical Co., Ltd.

Butyl acrylate ("BA") is available from The Dow Chemical Company.

Sodium p-Styrene Sulfonate ("SSS") and methyl acrylic acid ("MAA") are both available from Sinopharm Chemical Reagent Co., Ltd.

Silane coupling agent vinyl tri-methoxysilane ("A-171") is available from Momentive Chemical.

Branched alcohol ethoxylate based phosphate surfactant ("P-12A") is available from Solvay.

Sodium dodecyl (Linear) benzene sulfonate ("A-19"), available from Cognis, is used as a surfactant.

tert-butyl hydroperoxide ("t-BHP") and sodium persulfate ("SPS"), both available from Sinopharm Chemical Reagent Co., Ltd, are used as catalysts.

$FeSO_4 \cdot 7H_2O$ and ethylenediaminetetraacetic acid ("versene"), both available from Sinopharm Chemical Reagent Co., Ltd, are used as polymerization promoters.

Bruggolite FF6M ("FF-6"), available from Brueggemann Chemical, is used as an activator used in binder synthesis.

TERGITOL™ 15-S-40 ("15-S-40") and ECOSURF™ BD-109, both available from The Dow Chemical Company, are used as wetting agents (TERGITOL and ECOSURF are trademarks of The Dow Chemical Company).

Disponil FES-32 ("Fes-32"), is sodium salt of fatty alcohol ether sulphate, available from BASF, is used as surfactant.

OROTAN™ CA-2500 ("CA-2500") dispersant is available from The Dow Chemical Company (OROTAN is a trademark of The Dow Chemical Company).

NATROSOL 250 HBR thickener ("HBR") is available from Hercules Incorporated.

Sodium hydroxide ("NaOH") is available from Sigma-Aldrich.

TI-PURE R-996 pigment, available from DuPont, is titanium dioxide pigment.

TEGO Foamex 825 ("Tego-825") defoamer is available from Evonik Industries.

CC-700 extender ("CC-700") and Clay DB-80 are both available from Guangfu Building Materials Group.

Rhodoline FT100Xtrim ("FT-100XTRIM"), available from Solvay, is an anti-freezing-thawing agent.

Coasol 290 plus, available from Chemoxy International, is used as a coalescent.

SHC-2468 Flavor, available from International Flavors & Fragrances, is a flavor.

The following standard analytical equipment, test methods and synthesis process are used in the Examples.

Specific Surface Areas (BET Method)

Specific surface areas of adsorbent particles were determined by nitrogen ($N_2$) adsorption-desorption isotherms on a Micrometric ASAP 2010 apparatus. Samples were outgassed at 0.13 Pa and 100° C. for 6 hours prior to adsorption studies. The volume of gas adsorbed to the surface of the adsorbent particles was measured at the boiling point of nitrogen (−196° C.). The amount of adsorbed gas was correlated to the total surface area of the adsorbent particles including pores in the surface. Specific surface area calculations were carried out using the BET (Brunauer-Emmett-Teller) method.

Particle Size (D50)

The D50 particle size of adsorbent particles was measured using a Zetasizer nano ZS (Malvern Instrument, Inc., Worcestershire, UK) at a wavelength of 633 nm with a constant angle of 173° at room temperature. 5 milligrams (mg) of adsorbent particles were dispersed in 1 mL toluene before characterization. The equilibration time was 120 seconds, the cell used for the sample was PCS1115 glass cuvette, measurement duration mode was automatic, and number of measurement was one. The D50 particle size was obtained via the volume particle size distribution (PSD) page.

Particle Size Measurement (BI-90)

Particle size of polymer dispersions was measured by using Brookhaven BI-90 or 90Plus Particle Sizer, which employs the technique of photon correlation spectroscopy (light scatter of sample particles). This method involved diluting 2 drops of a polymer dispersion to be tested in 20 ml of 0.01 M NaCl solution, and further diluting the resultant mixture in a sample cuvette to achieve a desired count rate (K) (e.g., K ranging from 250 to 500 counts/sec for diameter in the range of 10-300 nm, and K ranging from 100 to 250 counts/sec for diameter in the range of 300-500 nm). Then the particle size of the polymer dispersion was measured and reported as an average diameter by intensity.

Fragrance Release Test 0.20 L micro-chamber was used for the g release test. 0.52 g of a paint formulation was brushed onto a round watch glass with a diameter of 4 centimeters (cm), then the glass was put in the micro-chamber under nitrogen atmosphere, and the cap of the micro-chamber was closed. The nitrogen flow passing through the micro-chamber was 70 ml/min. At the predetermined sampling point, Tenax TgA cartridge tubes (60/80, glass tube, Gerstel) were employed and time duration for each sampling was 30 minutes (flow rate: 50-70 mL/min, precisely measured using a flow meter). Total volume of collected gas sample was 1.5 L to 2.5 L. The Tenax TA cartridge tubes were then analyzed to determine the content of fragrance immediately by a Thermo Desorption (TDS) Gas Chromatography Mass Spectrometry (GC-MS) instrument using the following conditions:

(1) TDS GC-MS Instrument

A Gerstel thermo desorption system with TDS autosampler was coupled with an Agilent GC 7890-MSD 5975C.

GC Column: RXI-5MS column (30 meters (m)×0.25 millimeter (mm), 0.5 μm film); Carrier gas: helium carrier gas at 1.0 mL/min constant flow; and GC Oven program: 50° C., hold for 10 min, 5° C./min ramp to 250° C., hold for 5 min.

TDS parameters: A Gerstel cold injection system 4 (CIS-4) with programmable temperature vaporizing (PTV) injector was used for cryo-focusing the analytes prior to transferring the analytes to the analytical GC column. The temperature for TDS was from 20° C. (hold for 1 min) to 280° C. at 60° C./min (hold for 15 min). CIS-4 programming was from −150° C. (equilibration time: 1 min) to 280° C. at 12° C./s (hold for 5 min). Temperature of GC-MS transfer line was 280° C. Mass Spectrometry Detector (MSD) parameters (scan mode): MS Source temperature: 230° C., MS Quad temperature: 150° C., Acquire Mode: Scan, Mass 29-370 Da.

(2) Instrument Conditions for Quantification of Each Fragrance Compound

Quantification of each fragrance compound was conducted using MSD at Selective Ion Monitoring (SIM) mode:

Compound 1 (phenylethyl alcohol): 0-24.5 min; Mass, 57, 71, 91, 105, 122 Da, dwell time, 25 milliseconds (ms);

Compound 2 (limonene): 24.5-28.0 min; Mass, 91, 104, 121, 136 Da, dwell time, 25 ms;

Compound 3 ((2-methyl-2-propenyl)-benzene): 28.0-30.0 min; Mass, 82, 117, 123, 132 Da, dwell time, 25 ms;

Compound 4 (diphenyl ether): 30.0-34.0 min; Mass, 110, 141, 154, 170 Da, dwell time, 25 MS;

Compound 5 (benzenemethanol α-(trichloromethyl)-, acetate): 34.0-42.5 min; Mass, 107, 149 Da, dwell time, 50 ms; and Compound 6 (benzeneacetic acid, 2-phenylethyl ester): 42.5-55.0 min; Mass, 91, 104 Da, dwell time, 50 ms.

(3) Quantification of Fragrance Emitted from Different Samples in the Micro-Chamber Preparation of Flavor Standard:

The flavor standard of SHC 2468 flavor was prepared in an acetonitrile (ACN) solution (1000 μg/g). An aliquot of 4 μL of flavor standard was injected into a Tenax TA tube (60/80 mesh, Gerstel Co. ltd) to make a standard flavor tube. The charged ACN in the flavor standard tube was removed by a flow of helium (flow speed: 200 mL/min) passing through the Tenax TA cartridge for 10 minutes. Weight of each fragrance compound in the standard flavor tube, μg, was semi-quantified using the equation below:

$$W_{std\ fragrance} = TIC_{percent} \times C_{fragrance} \times V_{injected}$$

where $W_{std\ fragrance}$ is the weight of each fragrance compound in the flavor standard tube (μg); $TIC_{percent}$ is the percent of total ion chromatogram (TIC) of each fragrance compound in TDS GC-MS chromatogram of the flavor standard SHC 2468 by scan mode; $C_{fragrance\ std}$ is the concentration of the flavor standard SHC 2468 injected in the flavor standard tube, 1000 μg/g; and $V_{injected}$ is the volume of the flavor standard SHC 2468 injected in the Tenax tube, 4 μL.

Then, quantification of major fragrance compounds emitted from the sample by the micro-chamber method was conducted using the equation below:

$$C_{fragrance\ emitted} = Area_{SIM\ fragrance} / Area_{SIM\ std\ fragrance} \times W_{std\ fragrance} / V_{headspace}$$

where $C_{fragrance\ emitted}$ is the concentration each fragrance compound emitted from the sample (μg/m³); $A_{SIM\ fragrance}$ is the peak area of each fragrance compound in the sample Tenax tube (SIM mode); $A_{SIM\ std\ fragrance}$ is the peak area of each fragrance compound in the standard flavor tube (SIM mode); $W_{std\ fragrance}$ is the weight of a fragrance in the standard flavor tube (μg); and $V_{headspace}$ is the volume of gas collected in the sample Tenax tube (m³).

Sum of major fragrance concentrations emitted from the sample in the micro-chamber was used for evaluating the fragrance controlled release effects of such sample.

The total major fragrance concentration in SHC 2468 is 30.1%.

Total fragrance released for 336 hours (h) was calculated using the equation below:

$$\begin{aligned}W_{fragrance\ released} = &((C_{fragrance\ 5h}) \times 5 \pm \\&(C_{fragrance\ 5h} + C_{fragrance\ 24h}) \times (24-5)/2 + \\&(C_{fragrance\ 24h} + C_{fragrance\ 48h}) \times (48-24)/2 + \\&(C_{fragrance\ 48h} + C_{fragrance\ 144h}) \times (144-48)/2 + \\&(C_{fragrance\ 144h} + C_{fragrance\ 240h}) \times (240-144)/2 + \\&(C_{fragrance\ 240h} + C_{fragrance\ 336h}) \times (336-240)/2) \times \\&V_{chamber} \times (R_{air\ exchange\ rate} + 1),\end{aligned}$$

where $C_{fragrance\ t}$ is the concentration of total flavor emitted from the sample at the time t=n, n=5 h, 24 h, 48 h, 144 h, 240 h, 336 h; $R_{air\ exchange\ rate} = R_N \times T/V_{chamber}$; where $R_N$, the rate of nitrogen flow passing through the micro-chamber, is 70 ml/min; and T=60 min; and $V_{chamber}$, the volume of the micro-chamber, is 0.2 L.

Then, residual flavor (%) at 336 h was calculated using the equation below:

The residual flavor at 336 h (%) = $W_{fragrance\ released}$/($W_{fragrance\ put\ in\ chamber} \times 30.1\%$); where $W_{fragrance\ put\ in\ chamber}$ = Weight of paint put in chamber × Weight ratio of flavor in paint.

Synthesis of Binder (B001 Binder)

A monomer emulsion (ME) was prepared by mixing 914 grams (g) of BA, 548 g of ST, 23.9 g of MAA, 8.8 g of SSS, 4.9 g of A-171, 99.1 g of P-12A (25% active), 24.7 g of A-19 (19% active) and 343 g of deionized (DI) water, and then emulsified with stirring. Then, 854 g of DI water and 5.1 g of Fes-32 (32% active) were charged to a five-liter multi-neck flask fitted with mechanical stirring. The contents in the flask were heated to 84° C. under a nitrogen atmosphere. To the stirred flask, 1.6 g of Na₂CO₃ in 18.6 g of DI water, 50 g of ME with 40 g of rinse DI water, and 4.79 g of SPS in 16.4 g of DI water were added to the flask. The remaining ME and 1.63 g of SPS in 88 g of DI water were added gradually over 90 minutes. Reaction temperature was maintained at 80° C. Then, a neutralizer (1.99 g of sodium hydroxide in 44 g of DI water) was fed over 45 minutes. 32 g of DI water were used to rinse the monomer emulsion feed line to the flask. Thereafter, 6.93 g of FeSO₄.7H₂O (0.2% active) and 2.54 g of versene (1% active) were added into the reaction mixture. 1.92 g of t-BHP (70% active) in 20 g of DI water and 1.06 g of FF-6 in 20 g of DI water were shot into the flask. Then, 2.29 g of t-BHP (70% active) in 30 g of water, and 1.02 g of FF-6 in 30 g of water were fed into the flask over 30 minutes with agitation. The contents in the flask were cooled to room temperature. 11.4 g of 15-S-40 (70% active) and 1.07 g of sodium hydroxide in 29 g of DI water were feed over 15 minutes. 18 g of MEA in 18 g of DI water were added as neutralizer over 15 minutes to obtain the binder. The particle size (tested by BI-90) of the obtained binder was 120 nm, pH was 9.05, and solids content was 48.9%.

Synthesis of Flavor-Containing Binder (B002 Binder)

A flavor-containing binder was prepared according to the same procedure as preparing the Binder (B001) above, except that a flavor was added in the monomer emulsion prior to polymerization. The monomer emulsion used in preparing the B002 Binder was prepared by mixing 914 g of BA, 548 g of ST, 23.9 g of MAA, 8.8 g of SSS, 4.9 g of A-171, 99.1 g of P-12A (25% active), 24.7 g of A-19 (19% active), 11.3 g of SHC-2468 and 343 g of DI water, and then emulsified with stirring. The particle size (tested by BI-90) of the obtained binder was 124 nm, pH was 9.13, and solids content was 48.8%.

TABLE 1

Grinds Formulation

| Components | Weight (gram) |
| --- | --- |
| DI water | 300 |
| NATROSOL 250 HBR | 6 |
| CA-2500 | 18.75 |
| ECOSURF BD-109 | 3 |
| Tego-825 | 3 |
| TI-PURE R-996 | 150 |
| Clay DB-80 | 120 |
| CC-700 | 300 |
| NaOH | 1.08 |
| Grind sub-total | 903.75 |

Example (Ex) 1

SD-2 adsorbent was dried in an oven at 100° C. for 3 hours before grinding. 15 g of dried SD-2 adsorbent was added to a planetary ball mill and milled at 4,000 revolutions per minute (rpm) for 60 minutes, to give ground SD-2 adsorbent with D-50 particle size of 4.6 μm. 3.3 g of the ground SD-2 adsorbent was added to 100 g of B-002 Binder at 800 rpm for 20 minutes to form an aqueous binder dispersion. Based on formulations given in Table 1, 63.31 g of ingredients for preparing grinds were mixed using a high speed Cowles disperser to form the grinds. Then, 34.09 g of the above aqueous binder dispersion comprising ground SD-2 adsorbent and B-002 Binder, 0.35 g of SHC-2468 dispersant, 0.15 g of FT-100XTRIM anti-freezing-thawing agent, and 2.1 g of Coasol 290 coalescent were added to the grinds using a conventional lab mixer to obtain a paint formulation.

Ex 2

L493 adsorbent was dried in an oven at 100° C. for 3 hours before grinding. 15 g of dried L493 adsorbent was added to a planetary ball mill and milled at 4,000 revolutions per minute (rpm) for 60 minutes, to give ground L493 adsorbent with D-50 particle size of 2.1 μm. 3.3 g of the ground L493 adsorbent was added to 100 g of B-002 Binder at 800 rpm for 20 minutes to form an aqueous binder dispersion. Based on formulations given in Table 1, 63.31 g of ingredients for preparing grinds were mixed using a high speed Cowles disperser to form the grinds. Then, 34.09 g of the above aqueous binder dispersion comprising ground L493 adsorbent and B-002 Binder, 0.35 g of 15-S-40 dispersant, 0.15 g of FT-100XTRIM anti-freezing-thawing agent, 2.1 g of Coasol 290 coalescent were added to the grinds using a conventional lab mixer to obtain a paint formulation.

Comparative (Comp) Ex A 63.31 g of ingredients for preparing grinds, based on formulations given in Table 1, were mixed using a high speed Cowles disperser to form the grinds. Then, 32.9 g of B-001 Binder, 0.35 g of 15-S-40 dispersant, 0.15 g of FT-100XTRIM anti-freezing-thawing agent, 2.1 g of Coasol 290 coalescent, 1.09 g of water and 0.1 g of SHC-2468 flavor were added to the grinds using a conventional lab mixer to obtain a paint formulation.

Comp Ex B 63.31 g of ingredients for preparing grinds, based on formulations given in Table 1, were mixed using a high speed Cowles disperser to form the grinds. Then, 33 g of B-002 Binder, 0.35 g of 15-S-40 dispersant, 0.15 g of FT-100XTRIM anti-freezing-thawing agent, 2.1 g of Coasol 290 coalescent, and 1.09 g of water were added to the grinds using a conventional lab mixer to obtain a paint formulation.

Comp Ex C

Zeolite was dried in an oven at 100° C. for 3 hours before grinding. 15 g of dried zeolite was added to a planetary ball mill and milled at 4,000 revolutions per minute (rpm) for 60 minutes, to give ground zeolite adsorbent with D-50 particle size of 4.9 μm. 3.3 g of ground zeolite adsorbent was added to 100 g of B-002 Binder at 800 rpm for 20 minutes to form an aqueous binder dispersion. 63.31 g of ingredients for preparing grinds, based on formulations given in Table 1, were mixed using a high speed Cowles disperser to form the grinds. Then, 34.09 g of the above aqueous binder dispersion comprising ground zeolite adsorbent and B-002 Binder, 0.35 g of 15-S-40 dispersant, 0.15 g of FT-100XTRIM anti-freezing-thawing agent, 2.1 g of Coasol 290 coalescent were added to the grinds using a conventional lab mixer to obtain a paint formulation.

Comp Ex D

XAD1180 adsorbent was dried in an oven at 100° C. for 3 hours before grinding. 15 g of dried XAD1180 was added to a planetary ball mill and milled at 4,000 revolutions per minute (rpm) for 60 minutes, to give ground XAD1180 adsorbent with D-50 particle size of 2.9 μm. 3.3 g of the ground XAD1180 was added to 100 g of B-002 Binder at 800 rpm for 20 minutes to form an aqueous binder dispersion. 63.31 g of ingredients for preparing grinds, based on formulations given in Table 1, were mixed using a high speed Cowles disperser to form the grinds. Then, 34.09 g of the above aqueous binder dispersion comprising the ground XAD1180 adsorbent and B-002 Binder, 0.35 g of 15-S-40 dispersant, 0.15 g of FT-100XTRIM anti-freezing-thawing agent, and 2.1 g of Coasol 290 coalescent were added to the grinds using a conventional lab mixer to obtain a paint formulation.

Comp Ex E 63.31 g of ingredients for preparing grinds were mixed, based on formulations given in Table 1, using a high speed Cowles disperser to form the grinds. Then, 32.9 g of B-001 Binder, 0.35 g of 15-S-40 dispersant, 0.15 g of FT-100XTRIM anti-freezing-thawing agent, 2.1 g of Coasol 290 coalescent, 0.1 g of SHC-2468 flavor, and 1.09 g of ground L493 adsorbent with D50 particle size of 2.1 μm were added to the grinds using a conventional lab mixer to obtain a paint formulation.

Figure 1:
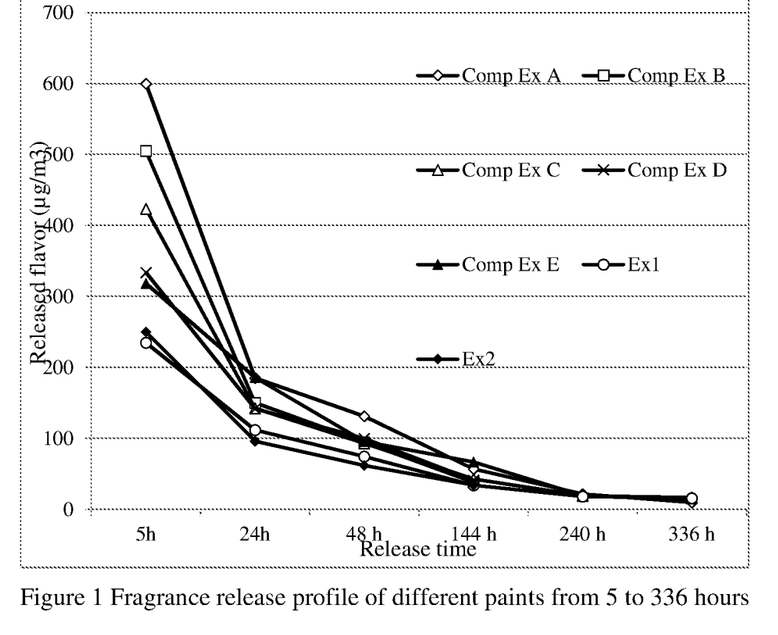
FIGS. 1 and 2 are fragrance release profiles of fragrance of paints from 5-336 hours and from 144-366 hours, respectively.
Figure 2:
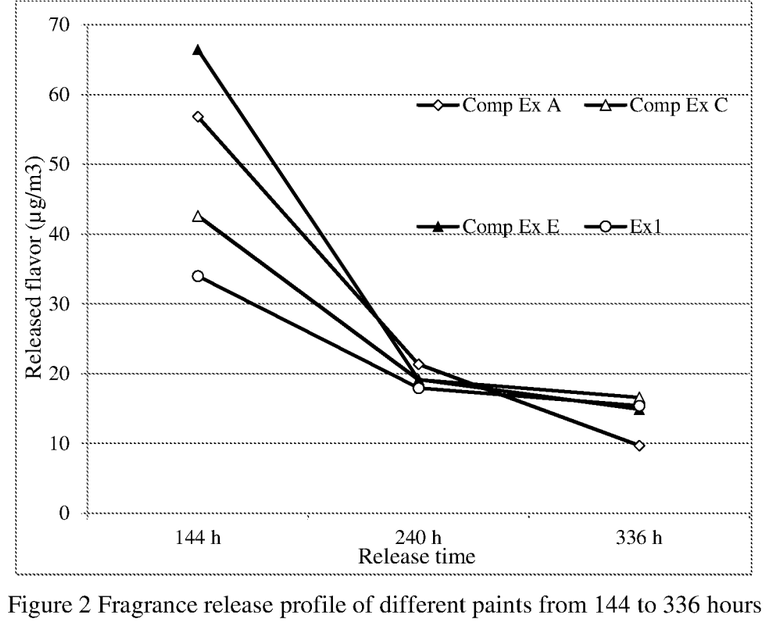

The above obtained paint formulations were evaluated for flavor release properties and results are given in Table 2 and FIGS. 1a and 1b. FIGS. 1a and 1b give release profiles of flavor of different paints during different period of time. The paint of Comp Ex A contained flavor post added to the binder. Incorporation of the flavor in the binder synthesis process retarded flavor release from paints (Comp Ex B) as compared to that of Comp Ex A. The paint of Comp Ex C contained ground zeolite and the flavor-containing binder. The paint of Comp Ex D included ground XAD1180 adsorbent and the flavor-containing binder. The paint of Comp Ex E contained flavor and ground L493 adsorbent both post added. Surprisingly, the combination of ground SD-2 or L493 adsorbent particles and a binder comprising fragrances added during polymerization resulted in better control release abilities of fragrance (Exs 1 and 2) than all Comp Exs A-E. Paints of Exs 1-2 demonstrated a slower fragrance release rate at the beginning, e.g., within initial 144 hours, the amounts of the fragrance released from paints of Exs 1 and 2 were significantly lower than that of Comp Ex A. In the meanwhile, the paint of Ex 1 also provided a continuous release of fragrance over a longer period of time, e.g., after 336 hours, the residual fragrance in Ex 1 was still 51%, while the residual fragrance for Comp Ex A, Comp Ex C, and Comp Ex E was only 15%, 35%, and 24%, respectively.

TABLE 2

Flavor release from containing paints comprising ground adsorbent

| Example | Adsorbent | Released flavor concentration (μg/m³) | | | | | | Released and residual flavor at 336 h | |
|---|---|---|---|---|---|---|---|---|---|
| | | 5 h | 24 h | 48 h | 144 h | 240 h | 336 h | Amount of flavor released (μg) | Amount of residual flavor (%) |
| Ex 1* | Ground SD-2 | 234.7 | 111.6 | 74.2 | 34.0 | 17.9 | 16.6 | 78.7 | 51% |
| Ex 2* | Ground L493 | 249.9 | 95.7 | 61.6 | 34.1 | n.d. | n.d. | n.d. | n.d. |
| Comp Ex A* | none | 599.4 | 185.1 | 131.0 | 56.8 | 21.3 | 9.7 | 136.8 | 15% |
| Comp Ex B* | none | 504.8 | 149.9 | 94.5 | 38.1 | n.d. | n.d. | n.d. | n.d. |
| Comp Ex C* | Ground Zeolite | 423.0 | 142.3 | 93.1 | 42.6 | 19.1 | 15.4 | 104.7 | 35% |
| Comp Ex D* | Ground XAD1180 | 333.6 | 141.8 | 99.7 | 41.0 | n.d. | n.d. | n.d. | n.d. |
| Comp Ex E** | Ground L493 | 318.0 | 185.6 | 95.5 | 66.4 | 19.1 | 14.9 | 121.3 | 24% |

*Flavor added in ME;
**flavor and Ground L493 both post added.

What is claimed is:

1. An aqueous dispersion, comprising:
   (a) fragrance-containing binder particles, and
   (b) polymeric adsorbent particles having a D50 particle size of from 1 to 30 microns and a specific surface area of 900 m²/g or more, wherein the polymer in the polymeric adsorbent particles comprises as polymerized units one or more vinyl aromatic monomers and optionally one or more monovinyl aliphatic monomers, and wherein the one or more vinyl aromatic monomers are selected from the group consisting of monovinyl aromatic monomers and polyvinyl aromatic monomers.

2. The aqueous dispersion of claim 1, wherein the polymeric adsorbent particles are present, by dry weight based on the dry weight of the fragrance-containing binder particles, in an amount of from 0.1% to 6%.

3. The aqueous dispersion of claim 1, wherein the fragrance-containing binder particles comprise, based on the dry weight of the fragrance-containing binder particles, from 0.0001% to 2% by dry weight of the fragrance.

4. The aqueous dispersion of claim 1, wherein the polymeric adsorbent particles have a specific surface area of 950 m²/g or more.

5. The aqueous dispersion of claim 1, wherein the polymeric adsorbent particles have a D50 particle size of from 1 to 15 microns.

6. The aqueous dispersion of claim 1, wherein the fragrance-containing binder is obtained by including the fragrance into a reactor at a temperature of 50° C. or above during preparation of the binder.

7. The aqueous dispersion of claim 1, wherein the fragrance-containing binder is obtained by polymerization of monomers in the presence of the fragrance.

8. The aqueous dispersion of claim 1, wherein the polymeric adsorbent particles comprise an alkylene bridged copolymer of divinylbenzene and a monovinyl aromatic monomer.

9. The aqueous dispersion of claim 1 having a PVC of less than 15%.

10. The aqueous dispersion of claim 1 wherein the binder particles have an average particle size of 50 to 500 nm.

11. The aqueous dispersion of claim 1 wherein the amount of polymeric adsorbent particles is 0.1 to 4 weight percent by dry weight.

12. The aqueous dispersion of claim 1 wherein the polymeric adsorbent particle comprises a porous cross-linked polymer.

13. The aqueous dispersion of claim 1 wherein the polymer in the polymeric adsorbent particles comprises an alkylene bridged cross-linked copolymer.

14. A process of preparing an aqueous dispersion, comprising:
  (i) providing fragrance-containing binder particles wherein the fragrance is included during preparation of the binder; and
  (ii) admixing the fragrance-containing binder particles obtained from step (i) with polymeric adsorbent particles having a D50 particle size of from 1 to 30 microns and a specific surface area of 900 $m^2/g$ or more, wherein the polymer in the polymeric adsorbent particles comprises as polymerized units one or more vinyl aromatic monomers and optionally one or more monovinyl aliphatic monomers, and wherein the one or more vinyl aromatic monomers are selected from the group consisting of monovinyl aromatic monomers and polyvinyl aromatic monomers.

15. The process of claim 14, wherein the fragrance-containing binder is obtained by polymerization of monomers in the presence of the fragrance.

16. An aqueous coating composition, comprising: the aqueous dispersion of claim 1 and a pigment.

17. A method of preparing an aqueous coating composition, comprising:
  admixing fragrance-containing binder particles with polymeric adsorbent particles to form an aqueous dispersion, wherein the polymeric adsorbent particles have a D50 particle size from 1 to 30 microns and a specific surface area of 900 $m^2/g$ or more, wherein the polymer in the polymeric adsorbent particles comprises as polymerized units one or more vinyl aromatic monomers and optionally one or more monovinyl alipathic monomers, and wherein the one or more vinyl aromatic monomers are selected from the group consisting of monovinyl aromatic monomers and polyvinyl aromatic monomers; and
  admixing the aqueous dispersion with a pigment.

* * * * *